(12) United States Patent
Grossman

(10) Patent No.: US 7,240,534 B2
(45) Date of Patent: Jul. 10, 2007

(54) DAMPER FOR HIGH G-FORCE SHOCK PULSE GENERATOR SYSTEMS AND METHODS

(75) Inventor: Owen D. Grossman, Golden Valley, MN (US)

(73) Assignee: Honeywell International Inc., Morristown, NJ (US)

( * ) Notice: Subject to any disclaimer, the term of this patent is extended or adjusted under 35 U.S.C. 154(b) by 70 days.

(21) Appl. No.: 11/144,494

(22) Filed: Jun. 2, 2005

(65) Prior Publication Data
US 2006/0272390 A1    Dec. 7, 2006

(51) Int. Cl.
*G01M 7/00* (2006.01)

(52) U.S. Cl. ............ 73/12.09; 73/12.01; 73/12.04; 73/12.07; 73/12.09

(58) Field of Classification Search ........... 73/12.09, 73/12.01, 12.04, 12.07
See application file for complete search history.

(56) References Cited

U.S. PATENT DOCUMENTS

| | | | | |
|---|---|---|---|---|
| 3,421,361 A | * | 1/1969 | Stowell | 73/12.07 |
| 3,739,625 A | * | 6/1973 | Roberts et al. | 73/12.07 |
| 3,836,757 A | * | 9/1974 | Nachtigal et al. | 702/41 |
| 4,426,683 A | * | 1/1984 | Kissell | 700/275 |
| 6,109,093 A | | 8/2000 | Albertini et al. | |
| 6,266,994 B1 | | 7/2001 | Albertini et al. | |
| 6,389,876 B1 | | 5/2002 | Tanimura et al. | |
| 6,655,190 B2 | | 12/2003 | Grossman et al. | |
| 7,007,540 B2 | * | 3/2006 | Koland et al. | 73/12.09 |

* cited by examiner

*Primary Examiner*—Michael Cygan
*Assistant Examiner*—Punam Patel
(74) *Attorney, Agent, or Firm*—Evan Bundis, Esq.; Armstrong Teasdale LLP

(57) ABSTRACT

The present invention provides systems and methods that can provide a high g-force to a test specimen. An exemplary system of the present invention includes a beam, rigidly fixed at one or both ends, on which a test specimen can be mounted. A loading device is preferably provided that can load the beam by using a ceramic column positioned between the beam and the loading device. A flywheel that has a cutter that can be deployed on command while the flywheel is rotating to fracture the ceramic column is also provided. The present invention also provides systems and methods for controllably damping the oscillation of a loaded beam at some point after the load on the beam is released to produce a high g-force event. For example, a damping device of the present invention may be engaged after the completion of the high g-force event. Such damping can prevent subsequent ringing or oscillation of the beam without affecting the magnitude of the high g-force event.

17 Claims, 17 Drawing Sheets

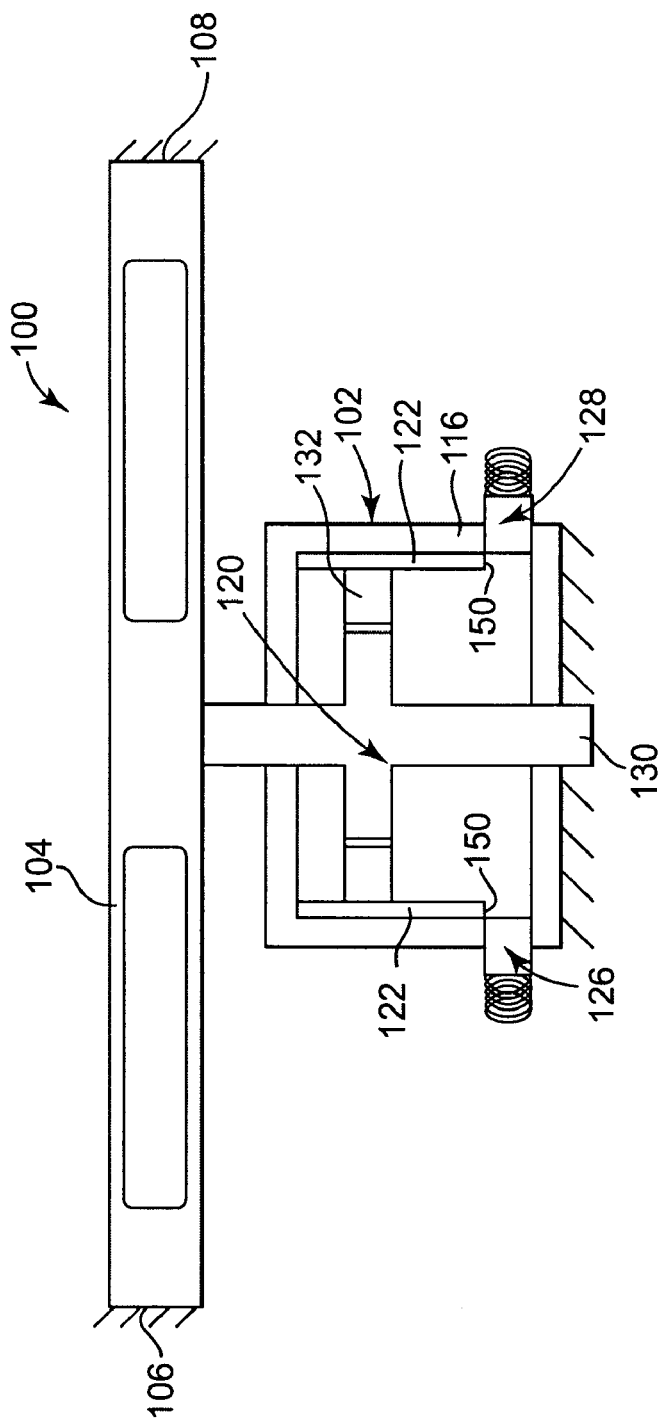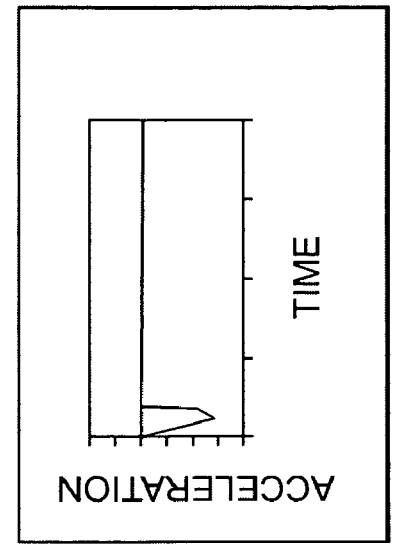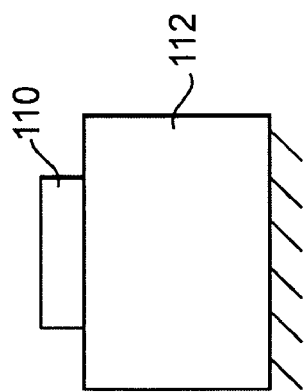
Fig. 11

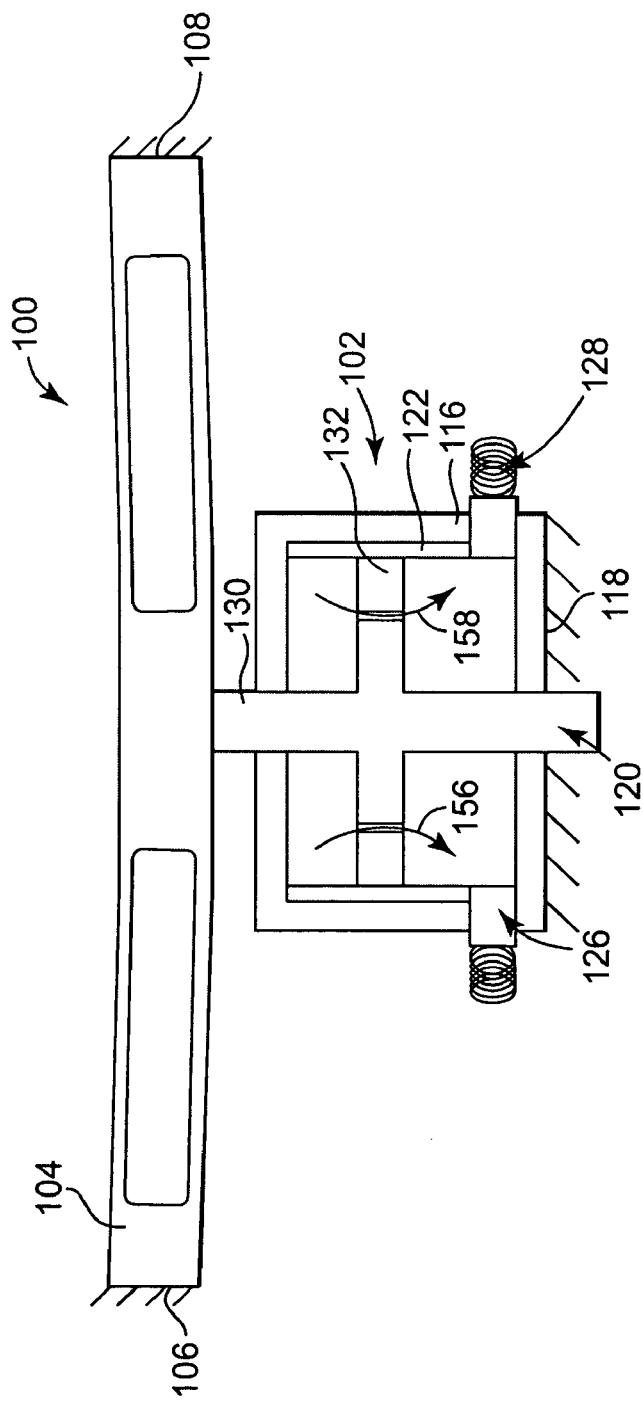
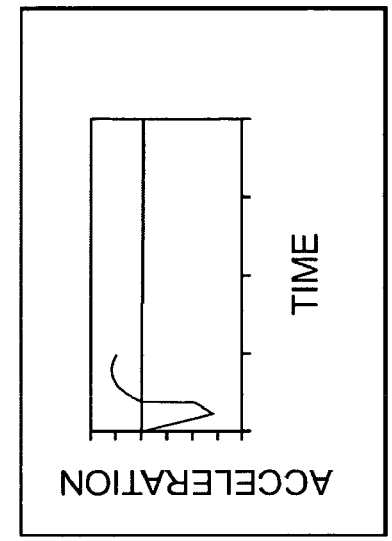
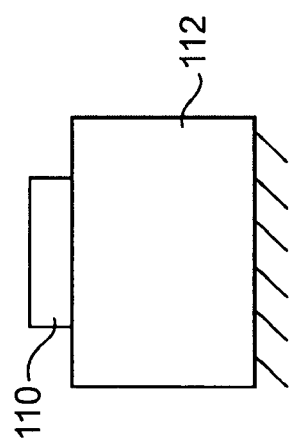
Fig. 14

DAMPER FOR HIGH G-FORCE SHOCK PULSE GENERATOR SYSTEMS AND METHODS

TECHNICAL FIELD

The present invention relates to systems and methods for subjecting a test specimen to a controlled impact or shock. More particularly, the present invention relates to systems and methods for providing a high g-force shock pulse to a test specimen.

BACKGROUND

Shock testing is used to characterize devices that are exposed to impact or shock in use. For example, electronic devices and components used in avionics applications such as gyroscopes and accelerometers can be exposed to shock in the form of high g-forces. Because of this, it is often desirable to characterize the effect of such high g-forces on such devices as part of the design process.

One shock testing technique for applying a high g-force shock to a test specimen is disclosed in U.S. Pat. No. 6,655,190 to Grossman et al., which is fully incorporated herein by reference for all purposes. The device and method of Grossman et al. uses a test system that includes an I-beam fixed at one or both ends. A test specimen is mounted to the beam and electrically connected to a monitoring system to record or monitor the effects of the high g-force shock provided to the test specimen during the test. The beam is loaded within the elastic range of the beam material by applying a force that deflects the beam away from a static position by a predetermined amount. Such loading creates a high strain on the beam and stores elastic energy in the beam. The high g-force event is created by suddenly releasing the stored energy in the beam by removing the force. A shockwave travels along a length of the test beam and applies a high g-force to the test specimen.

In order to create a high g-force in this way, it is desirable to release the loading of the beam suddenly and reliably. Releasing the beam suddenly contributes to maximizing the g-force that can be achieved for a particular beam and loading condition. This is because the length of time that it takes to completely remove the loading force from the beam can contribute to a decrease in the elastic energy that creates the high g-force event. Thus, when a sudden release is achieved, more of the elastic energy that is stored in the beam can efficiently contribute to the high g-force event.

Releasing the beam in a reliable manner relates to a desire to provide consistency and repeatability in testing. For certain test specimens, such as inertial devices for example, it is desirable to minimize any forces that might act on the beam from directions other than the desired or primary direction of the applied g-force. In order to do this, the force applied to the beam needs to be repeatedly released in a controlled and reliable manner. The need to have a clean and repeatable test is important for most test devices. If the test is repeatable then the relationship between the motions in various directions is fairly consistent. By monitoring motion in the primary direction there is reasonable confidence that the motion in the other directions stays within some limits. If the motion is primarily in one direction it is easier to determine the cause and effect relationship between the shock applied and the resulting behavior of the test specimen (breakage, shift in performance, etc.). Also, in order to be able to meaningfully compare test results from plural test runs, consistency throughout the test runs is desired. Reliability in testing is also desired because test specimens can be expensive or their availability may be limited. As such, it is undesirable for a test to fail. Moreover, shocking a test specimen with a g-force that is lower than the desired test force can make the test specimen unsuitable for further testing. Thus, for many applications, test specimens must be tested at the desired g-force on the first test run.

The Grossman et al. test device uses a hydraulic ram to apply the loading force to the beam. In particular, the ram applies the loading force to a ceramic column that is positioned between the ram and the beam. In this condition, the ceramic column is put in compression and supports the complete load directed to the beam. In order to conduct the test and cause a sudden beam release and thus create the high g-force event, the ceramic column is impacted with a projectile to fracture the ceramic column and quickly release the beam, thereby creating a high g-force event. This technique effectively releases the beam in a sudden and reliable manner. However, where it is desired to increase the g-force created by the test, an increased load is placed on the beam by the hydraulic ram through the ceramic column to provide greater stored elastic energy in the beam. In order to support the increased load, the diameter of the ceramic column is increased. The ceramic column thus experiences a correspondingly increased load and greater energy is required to be provided by the projectile to fracture the ceramic column because of its increased diameter. Where the ability to provide a projectile with sufficient energy is unavailable or difficult, other techniques that can suddenly and reliably fracture the ceramic column are desired.

After the force is removed from the beam and the high g-force event is completed, the beam will resonate until the energy stored in the beam is fully dissipated. The magnitude of the g-force is greatest during the first resonant cycle of the beam and it is the reaction of a test specimen to this maximum g-force that is usually of most interest. Subsequent resonance of the beam may be undesirable for certain applications. Such ringing can be undesirable where the purpose of a test is to simulate a real world shock event such as a gun launch or the like as accurately as possible. Repeated oscillations after the primary shock event are generally unrealistic and could conceivable cause damage to a test specimen that would not occur as a result of an actual real world shock event. Also, by eliminating the ringing it is easier to demonstrate by analysis of the data that a real world shock event has been adequately simulated.

SUMMARY

The present invention therefore provides systems and methods for controllably damping the oscillation of a loaded beam at some point after the load on the beam is released to produce a high g-force event. For example, a damping device of the present invention can be engaged after the completion of a predetermined portion of the high g-force event. Such damping can prevent subsequent ringing or oscillation of the beam without affecting the magnitude of the high g-force event.

Accordingly, in one aspect of the present invention, a method for applying a high g-force to a test specimen is provided wherein a damper is engaged at a predetermined point after the high g-force event. This method generally includes the steps of rigidly fixing at least one end of a beam, mounting a test specimen on the beam, applying a force to the beam with a loading device, releasing the force, and positively engaging a damper at a predetermined point after releasing the force. Preferably, the test specimen is mounted on the beam at a predetermined location with respect to the rigidly fixed end of the beam. The force is preferably applied at a predetermined location with respect to the rigidly fixed end of the beam to elastically strain the beam by a predetermined amount. The step of applying a force to the beam may include positioning a breakable loading member between the loading device and the beam and impacting the breakable loading member with a cutter. For example, a cutter can be radially extended from a flywheel to break the breakable loading member to release the force applied to the beam by the loading device.

In another aspect of the present invention, a system for applying a high g-force to a test specimen is provided. Generally, the system includes a beam, a loading device, means for controllably releasing a load provided to the beam by the loading device, and a damper. The beam is preferably rigidly fixed at an end and can have a test specimen mounted on the beam at a predetermined location from the rigidly fixed end of the beam. Preferably, the loading device can apply a force to the beam at a predetermined location with respect to the rigidly fixed end of the beam. The means for controllably releasing the load can include a breakable loading member that can be positioned between the loading device and the beam to apply the force to the beam. An impacting device can be used to impact the breakable loading member when the breakable loading member is positioned between the loading device and the beam. For example, the impacting device may include projectiles and the like as well as the use of explosive bolts and the like. Preferably, the damper is positively engageable at a predetermined point after the force applied to the beam is released.

BRIEF DESCRIPTION OF THE DRAWINGS

These and other features, aspects, and advantages of the present invention will become better understood with regard to the following description, appended claims, and accompanying drawings where:

FIG. 11 shows a second portion of the first half-cycle of the motion of the test beam wherein the damping device is engaged at the completion of the first half-cycle of the motion of the test beam;

FIGS. 14 and 15 show the third half-cycle of the motion of the test beam with the damping device engaged and providing a damping function.

DETAILED DESCRIPTION

Figure 1:
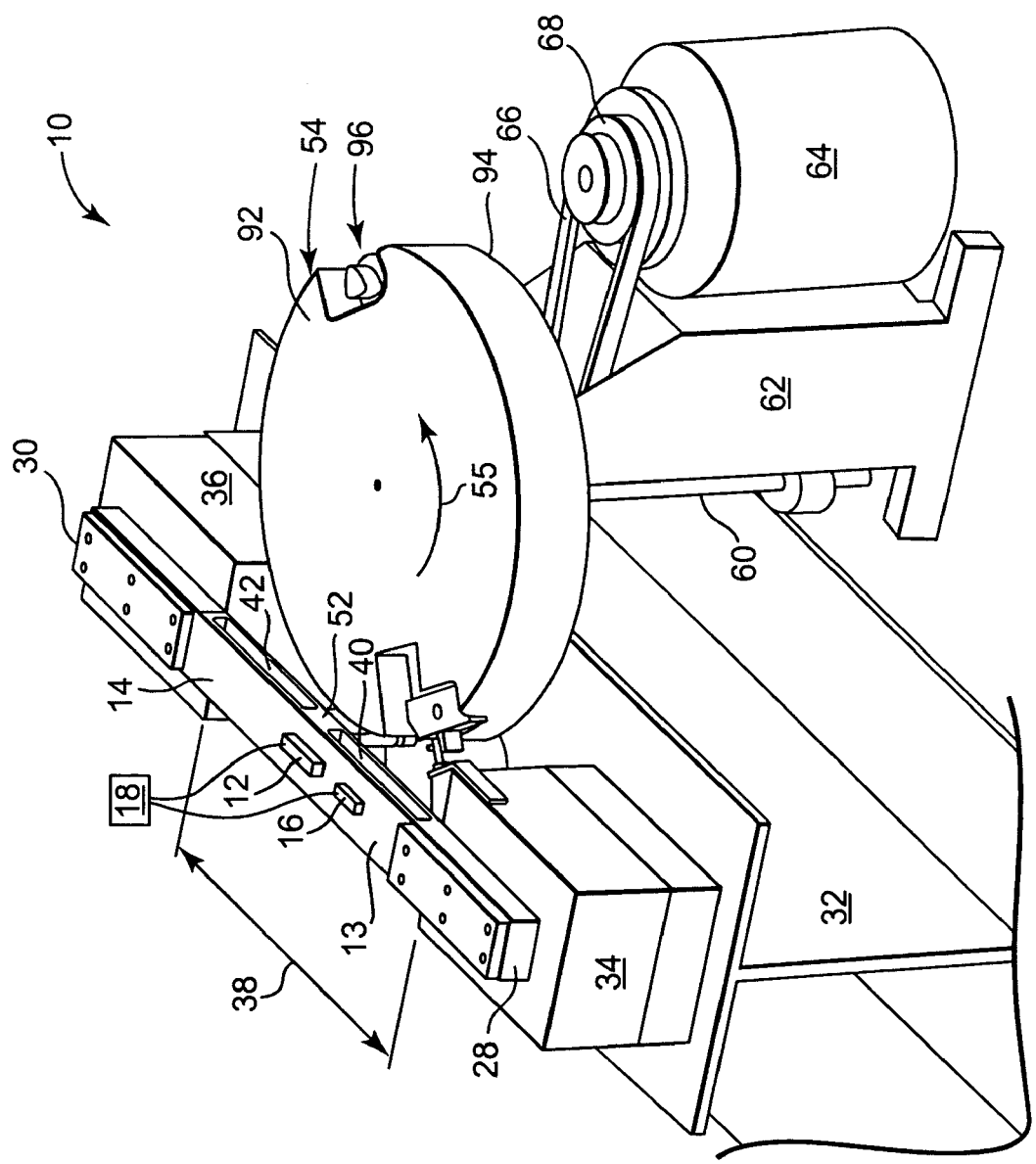
FIG. 1 is a perspective view of a system in accordance with the present invention comprising a flywheel having a radially extending cutter that can be used to suddenly release a loaded test beam having a test specimen provided thereon.
Figure 2:
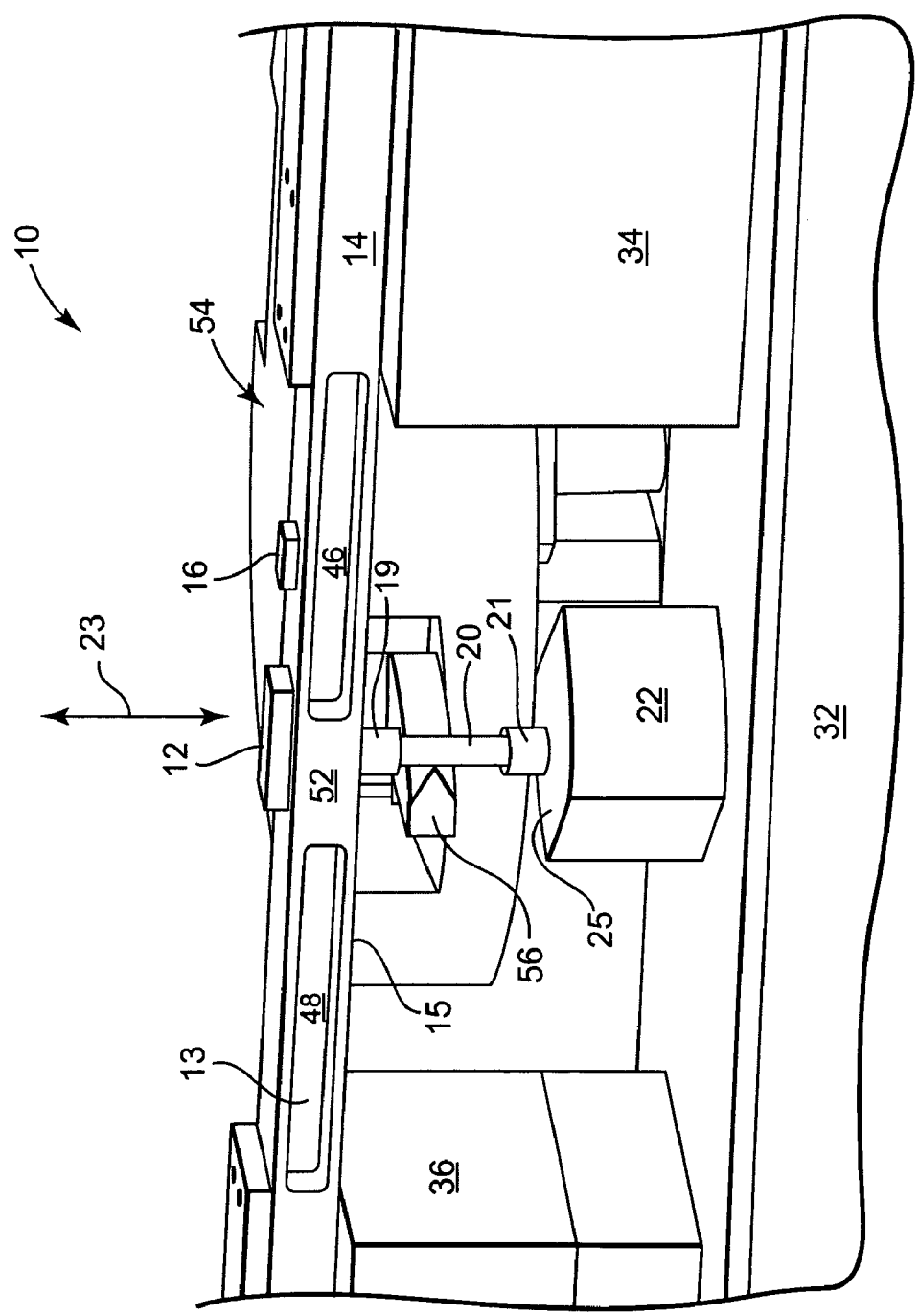
FIG. 2 is a perspective view of the system of FIG. 1 wherein the cutter is shown in an extended position just prior to impacting a breakable member that is loading the test beam with a loading device.

Referring to FIGS. 1 and 2, a system 10 that can be used to apply a high g-force to a test specimen 12 is shown. As illustrated, the test specimen 12 is provided on a test beam 14 along with a sensor 16 that can communicate with a control system 18 that can be used to control certain aspects of the operation of the system 10 as described below. Preferably, the test specimen 12 is mounted to a top surface 13 of the test beam 14, as illustrated. A breakable member 20 is positioned between the test beam 14 and a loading device 22. The loading device 22, through the breakable member 20, provides a predetermined load on the test beam 14 along a loading axis 23. To conduct the test, the load on the test beam 14 is preferably released by impacting the breakable member 20 with a cutter 56 that radially extends from a rotating flywheel 54. When the predetermined load on the test beam 14 is high enough, abruptly releasing the load on the test beam 14 in this way can subject the test specimen 12 to a high g-force event. During the test, the control system 18, which preferably includes data acquisition capability, can be used to record information from the sensor 16 and/or the test specimen 12 as described in more detail below.

The test specimen 12 may include devices such as accelerometers, gyroscopes, and other electronic components. Parameters that can be tested relate to the fragility and mechanical and electrical integrity of a particular test specimen. Any property, operating parameter, or design specification of a test device may be monitored or measured before, during, and after application of a high g-force event in accordance with the present invention. The present invention can be used to evaluate the ability of a test specimen to perform a particular function or accomplish a particular mission during or following a high g-force event or environment. If it is determined that the a test specimen can not perform a particular function or accomplish a particular mission the present invention can be used to perform experiments (shock testing) to characterize and determine the nature of the test specimen's design deficiency.

As shown in FIG. 1, first and second ends, 28 and 30, of the test beam 14 are each attached to an I-beam 32 with first and second support structures, 34 and 36, respectively. However, it is noted that the system 10 can be designed to have a cantilevered test beam wherein a single end of the test beam is fixed. When a system that has a test beam fixed at both ends is used, such as the illustrated system 10, a test span 38 for the test beam 14 is defined. The test span 38 of the test beam 14 is the portion of the test beam 14 that is free and not otherwise restrained by the support structures, 34 and 36. The length of the test span 38 of the test beam 14 can be determined by considering factors such as the material of the test beam 14, the cross-sectional geometry of the test beam 14, and the desired magnitude of a g-force to be provided by the test beam 14, for example. Other design factors for the test beam 14 are set forth and described further below. A cantilever test beam can be designed in a similar manner The test beam 14 is preferably designed to maximize the amount of energy that can be stored in the test beam 14 when a given load is applied to the test beam 14 by any force applying technique, preferably by the breakable member 20 and the loading device 22. In order to do this, the test beam 14 is preferably designed to minimize the weight of the test beam 14, maximize the strength of the test beam 14, and maximize the ability of the test beam 14 to flex without permanent deformation. The force applied to the beam is roughly proportional to the amount of deflection of the beam. Preferably, in accordance with the present invention a relatively slow beam motion (i.e. low frequency oscillation) is used. There is a direct correspondence between maximizing the deflection for a given applied force and minimizing the rate of the motion.

One factor in the design of the test beam 14 is the material used. The test beam 14 is preferably made from a material that comprises high strength, a high yield point, and good machinability. The material used for the test beam 14 is also preferably economical and readily available. Exemplary materials include high strength aluminum and aluminum alloys as well as titanium and titanium alloys. One preferred material for the test beam 14 is 6AL4V titanium as conventionally designated and commercially available. This material provides a good compromise involving cost, availability and material properties. Any known or future developed high yield point materials and alloys may be used. Moreover, the use of composite structures comprising plural different materials is contemplated.

Another factor in the design of the test beam 14 relates to the geometry of the test beam 14. As shown, the exemplary test beam 14 preferably includes spaced apart pockets, 40 and 42, that are provided from a first side 44 of the test beam 14 (see FIG. 1) and spaced apart pockets, 46 and 48, that are provided in a second side 50 of the test beam 14 (see FIG. 2). The pockets, 40 and 46, are preferably oppositely facing and aligned to each other and the pockets, 42 and 48, are also preferably oppositely facing and aligned to each other. When designed this way, the pockets, 40 and 46, and the pockets, 42 and 48, define a cross-sectional geometry for the test beam 14 that is similar to that of an I-beam wherein the I-shape extends longitudinally. Such a cross-sectional geometry can provide reduced weight without sacrificing strength.

Spacing the pockets, 40 and 46, apart from the pockets, 42 and 48, defines a generally solid portion 52 of the test span 38 of the test beam 14, as illustrated. The solid portion 52 is designed to receive the test specimen 12 and may include mounting holes or fixturing for attaching the test specimen 12 to the solid portion 52 of the test beam 14. The solid portion 52 also functions to provide a rigid region for loading the test span 38 of the test beam 14.

As illustrated in FIG. 2, for example, the breakable member 20 preferably includes end caps, 19 and 21, that function to distribute the pressure placed on a surface 25 of the loading device 22 and a bottom surface 15 of the test beam 14. One exemplary end cap design comprises a solid calendar that is about 0.5 inches in diameter and 0.38 inches high. Such end caps are preferably formed from a hard material such as tool steel or the like. For example, 0.5 inch diameter drill rod can be used to form such end caps. An exemplary breakable member is preferably about 0.31 inches in diameter so the end caps provide a bit more than twice the bearing area of the breakable member. The breakable member 20 preferably comprises a material that can be fractured in a way that suddenly releases the load on the test beam 14 when impacted with the cutter 24. Preferably, the breakable member 20 comprises a ceramic material such as alumina (aluminum oxide), preferably pure, or the like. Alumina is readily commercially available and relatively inexpensive. Alternative materials that can be used include zirconium oxide and tungsten carbide.

As illustrated, the breakable member 20 comprises a uniform cylindrical column having a circular cross-section. The cross-section of the breakable member 20 does not need to be circular however, and can comprise any desired shape as long as the breakable member 20 functions in accordance with the present invention. Moreover, the cross-sectional shape of the breakable member 20 can vary along the length of the breakable member 20 and does not need to be uniform. In any case, the breakable member is preferably designed to comprise a compressive strength sufficient to load the test beam 14 in accordance with the present invention. Preferably, the breakable member 20 comprises a compressive strength in excess of about 300,000 pounds per square inch (psi).

The loading device 22 may comprise any known or future developed device, mechanism, or machine capable of controllably providing a force in accordance with the present invention. Preferably, a hydraulic cylinder is used. Alternatives include screw jack, air jack, or ratchet jack type devices/mechanisms.

One aspect of the present invention is the ability to quickly and reliably release a test beam as loaded for providing a high g-force to a test specimen. As noted in the Background section, the use of a breakable member as a force transfer element is one preferred approach used to elastically strain a test beam. In order to release the loaded beam reliably, the breakable member needs to be impacted with a consistent predetermined force sufficient to fracture the breakable member and suddenly release the force on the beam. The present invention takes advantage of the energy provided in a moving body without having to put the body in motion near the time of impact. The present invention provides a continuously moving body that is caused to move at a speed sufficient to provide the required energy for fracturing the breakable member in a way that suddenly and reliably releases the load on the beam to create the high g-force event. A breaking element or cutter associated with the continuously moving body can be activated or deployed on command in accordance with the present invention. In this way, the breaking element can be activated and controlled with precision to cause the breakable member to fractured at the right time for releasing the load on the beam suddenly and reliably.

Referring to FIG. 1 in particular, the system 10 comprises a flywheel 54 having a controllably deployable cutter 56 that can be deployed on command to fracture the breakable member 20 and release the loaded test beam 14. As described further below, the cutter 56 can be deployed with a trigger 58 that is functionally mounted to the first support structure 34 as the flywheel 54 rotates in a drive direction 55 (counterclockwise in FIG. 1). The flywheel 54 is preferably connected to a drive shaft 60, which drive shaft 60 is supported by a frame structure 62 with suitably designed bearings as described below. In this configuration, the flywheel 54 is operatively supported and positioned relative to the breakable member 20 by the drive shaft 60 as supported by the frame structure 62.

As shown, a motor 64 is mounted to the frame structure 62 and is configured to drive the drive shaft 60 by a belt 66 that is provided between a pulley 68 of the motor 64 and a pulley (not viewable in the Figures) that is functionally integrated with the drive shaft 60. Preferably an electric motor is used for the motor 64 but any motor capable of functionally causing the flywheel 54 to rotate in accordance with the present invention can be used. Moreover, the illustrated drive train described above comprising the motor 64, belt 66, pulley 68, and the pulley of the drive shaft 60 that is not viewable in the Figures is merely exemplary and other drive techniques can be used to drive the flywheel 54 in accordance with the present invention. For example, a motor can be coupled to the drive shaft 60 with a gearbox or the like. Other examples include a friction drive wheel pressing directly on the circumference of the flywheel.

Figure 3:
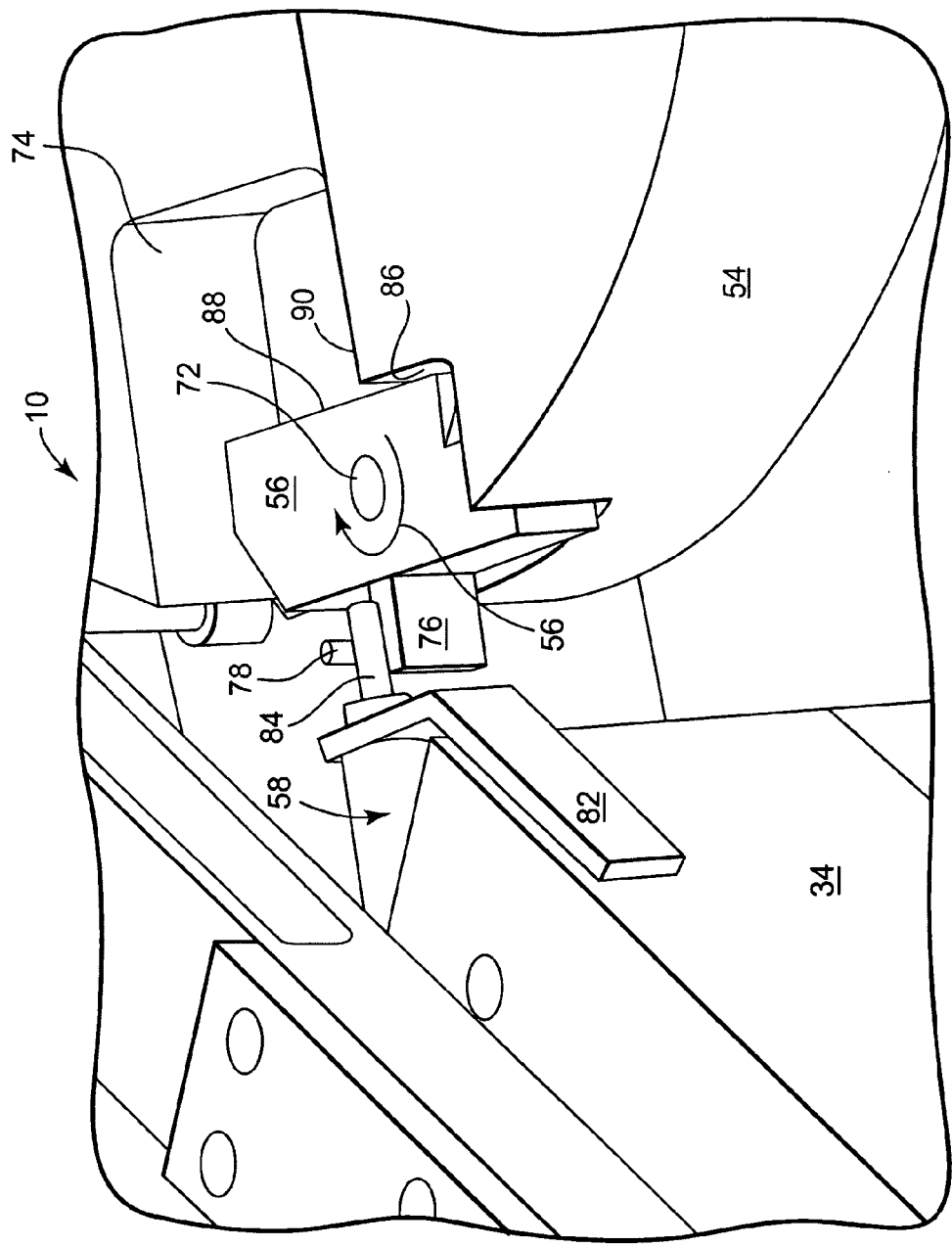
FIG. 3 is a perspective view of the cutter of the flywheel of the system of FIG. 1 shown in a retracted position wherein an arm of a trigger is shown in an extended position to impact with an arm of the cutter to toggle the cutter into an extended position.
Figure 4:
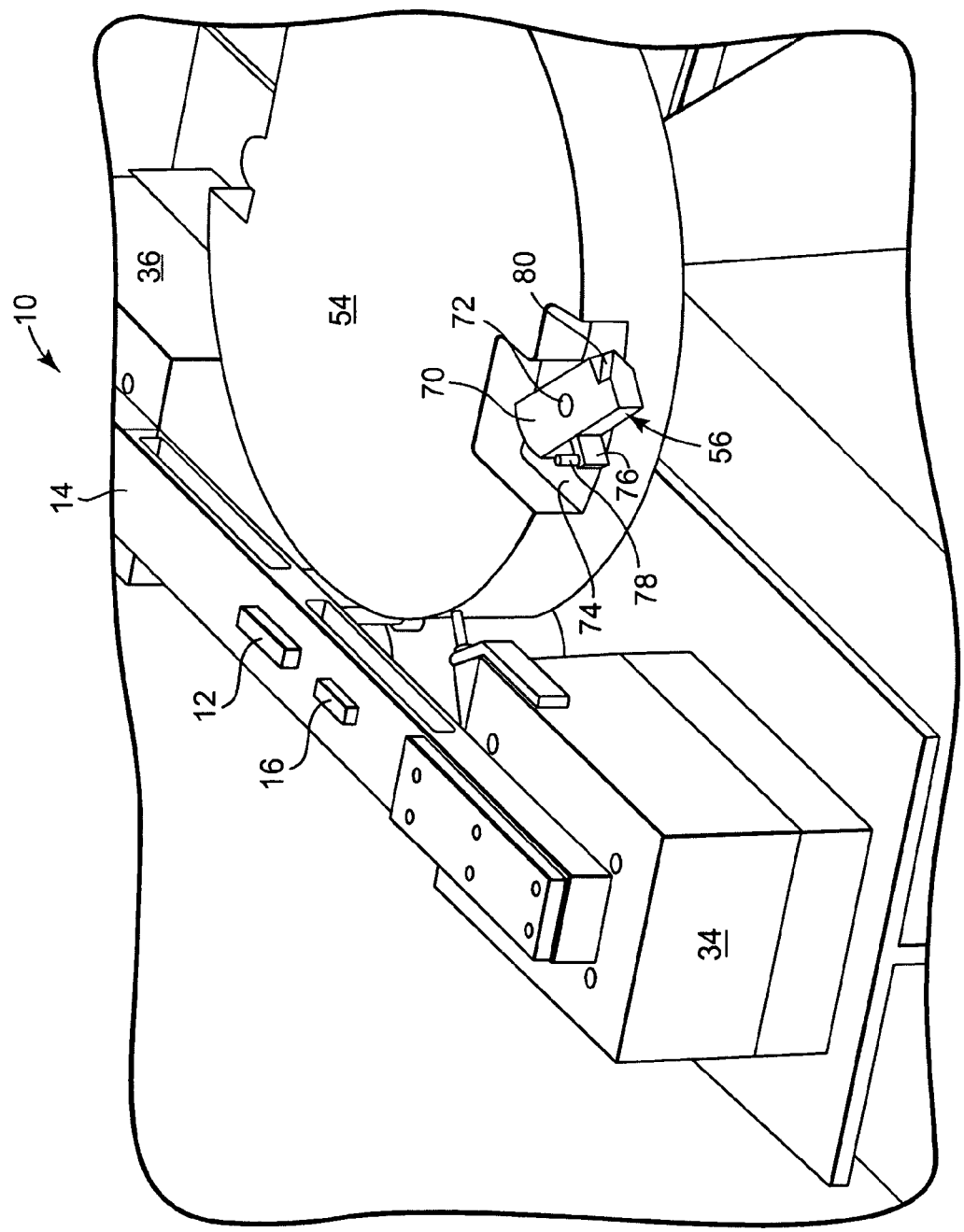
FIG. 4 is a perspective view of the flywheel shown in FIG. 3 after the arm of the trigger has impacted the arm of the cutter to extend the cutter, but where the cutter is only partially rotated between the retracted position shown in FIG. 3 and an extended position as shown in FIG. 2.

Referring to FIGS. 2-4, the cutter 56 and trigger 58 can be described in greater detail. FIG. 3 shows the cutter 56 in a retracted position just before the cutter 56 is deployed by the trigger 58 as the flywheel 54 rotates in the drive direction 55. The cutter 56 is shown partially deployed in FIG. 4 and in FIG. 2 the cutter 56 is shown in a fully deployed position just as the cutter 56 is about to impact the breakable member 20. As illustrated in FIG. 4, the cutter 56 comprises a body portion 70 that is pivotably mounted to the flywheel 54 at a pivot point 72 within a recessed region 74, the function of which is described below. An extension portion 76 of the cutter 56 includes a toggle arm 78 that is designed to work together with the trigger 58 to cause the cutter 56 to rotate about the pivot point 72 as described below. The cutter 56 also includes an impacting portion 80 that is designed to break the breakable member 20 and is also described in more detail below.

Referring to FIG. 3 in particular, the trigger 58 is preferably mounted to the support structure 34 by a bracket 82. As shown, the trigger 58 comprises a solenoid having a trigger arm 84 that can be extended and retracted under the control of the control system 18. However, the system that controls the solenoid may be separate from the control system 18. The trigger 58 may comprise any device or mechanism that is capable of cooperatively functioning with the cutter 56 to controllably deploy the cutter 56 on command in accordance with the present invention.

The cutter 56 is preferably mounted to the flywheel 54 with a pivot mechanism (not shown). The pivot mechanism is preferably designed so that the cutter 56 can rotate in a rotational direction 57 that is opposite the drive direction 55 of the flywheel 54 (clockwise in FIG. 3). The axis of rotation of the cutter 56 is preferably designed to be parallel to the axis of rotation of the flywheel 54. Additionally, the cutter 56 is preferably designed so that the pivot point 72 is located at the center of gravity of the cutter 56 or so that the cutter is otherwise balanced about the pivot point 72. The pivot point 72 of the cutter 56 is also preferably positioned near the outside diameter of the flywheel 54. The cutter 56 and pivot mechanism are designed so that the cutter 56 can rotate into a position where the impacting portion 80 of the cutter 56 can impact and break the breakable member 20 as shown in FIG. 1. Preferably, when the cutter 56 is in the retracted position, the cutter is substantially positioned within the outside diameter of the flywheel 54.

In order to function in this way, the pivot mechanism preferably comprises a pivot pin and one or more bearings that allow the cutter to rotate relative to the flywheel 54. The pivot mechanism also preferably functions as an over-center mechanism and preferably comprises an over-center spring or the like to provide such functionality. An over-center mechanism functions to provide a bias for positively engaging a device into alternate engagement positions. As used in accordance with the present invention an over-center mechanism provides the cutter 56 with the capability to positively toggle into positive engagement with the extended position shown in FIG. 2 and the retracted position shown in FIG. 3. An over-center mechanism is an exemplary device for biasing the cutter 56 into its extended and retracted states. Any known or future developed functionally equivalent device or mechanism that can bias the cutter 56 into its extended and retracted states in accordance with the present invention can be used.

When the cutter 56 is in the retracted position illustrated in FIG. 3, the pivot mechanism preferably positively drives the impacting portion 80 of the cutter 56 to seat against a surface portion 86 of the recessed region of the flywheel 54. The surface portion 86 thus functions to limit the rotation of the cutter 56 under the action of the spring force provided by the pivot mechanism. This spring force is preferably provided by an over-center spring as mentioned above.

When the cutter 56 is in the extended position illustrated in FIG. 2, the pivot mechanism preferably positively drives a side surface 88 of the cutter 56 to seat against a surface portion 90 of the recessed region 74 of the flywheel 54. As with the surface portion 86 described above the surface portion 90 also functions to limit the rotation of the cutter 56 under the action of the spring force provided by the pivot mechanism.

The cutter 56 does not need to be mounted within the recessed region 74 as illustrated in the Figures. The cutter 56 could be mounted to either of a top surface 92 or bottom surface 94 of the flywheel 54. If designed in this way, the surface portions, 86 and 90, could be functionally replaced with any suitable hard stop such as a pin or extension portion of a surface of the flywheel 54. In any event, the flywheel 54 with the cutter 56 installed is preferably designed so that the flywheel 54 is balanced in both the retracted and extended positions of the cutter 56. This is preferably done by forming a cutout region 96 in the flywheel 54, if needed, as can be seen in FIG. 1, for example. Preferably, the flywheel 54 is also balanced by designing the cutter 56 so that the pivot point 72 passes through the center of mass of the cutter 56. It is also preferable that the center of mass of the over-center spring does not move appreciably as a result of the triggering event.

The flywheel 54 and the manner in which the flywheel 54 is supported and driven are preferably designed so that the flywheel 54 can be rotated at a sufficient speed to provide sufficient energy to the cutter 56 for breaking the breakable member 20 in accordance with the present invention. That is, the cutter 56 is preferably capable of breaking the breakable member 20 to release the load on the test beam 14 suddenly and in a way that minimizes or eliminates any forces that could act on the test beam 14 in a direction other than that desired. In order to do this, the breakable member 20 is preferably fractured without upsetting the motion of the test beam 14. Preferably, the speed of the flywheel 54 is maintained throughout the fracture of the breakable member 20.

One exemplary flywheel that can be used as the flywheel 54 in accordance with the present invention comprises a steel disk (mild steel, for example) having a diameter of about 11.5 inches and a thickness of about 2 inches. An exemplary cutter that can be used as the cutter 56 comprises a steel bar that is about 3 inches long, 1 inch wide, and 0.5 inches thick. Preferably, a hardenable tool steel or the like is used. This exemplary flywheel and cutter design are preferably arranged so that the pivot point of the cutter is about 5 inches from the center of rotation of the flywheel. IN this exemplary arrangement, the breakable member is positioned about 6.3 inches from the center of rotation of the flywheel. Preferably, the cutter 56 is designed so that the cutter 56 is balanced so that the pivot point 72 passes through the center of gravity of the cutter 56. The radius on the impact edge of the cutter 56 is preferably designed to compromise between a smaller radius for improved breaking of the column versus a larger radius to improve the durability of the cutter. That is, a sharper edge cuts better buts becomes dull sooner than a larger radius. As an example, a radius between about 0.01 inches and about 0.10 inches can be used. A radius of about 0.06 inches provides a good compromise between cutting effectiveness and durability. The pivot point 72 is designed to have sufficient cross sectional area and be of sufficient strength to absorb the force of the impact with the column. In this exemplary embodiment of a flywheel and cutter, the cutter 56 is preferably integrated with the flywheel 54 by using an over-center mechanism that provides about 5 inch-pounds (force) of average torque. The drive train for this exemplary flywheel is preferably designed so that the flywheel can be rotated at speeds in excess of 1500 RPM's, more preferably 1750 RPM's, and even more preferably 2000 RPM's. Preferably, at a speed of about 1750 RPM's this exemplary flywheel can store in excess of 20,000 inch-pounds (force) of energy. Also, at a speed of about 1750 RPM's the breakable member 20 can preferably be fractured in under 0.3 milliseconds.

In use, the test specimen 12 is preferably mounted to the top surface 13 of the test beam 14 and generally above the solid portion 52 of the test beam 14 as shown in FIG. 1, for example. Moreover, the test specimen 12 is preferably positioned with respect to the loading axis 23 in a predetermined manner. For example, the test specimen 12 can be positioned on the test beam 14 so that a predetermined axis of the test specimen 12 is parallel and coincident with the loading axis 23, parallel and spaced from the loading axis 23, at an angle to and passing through the loading axis 23, or at an angle to and spaced from the loading axis 23. The test specimen 12 can be provided on the test beam 14 in any desired manner including the use of fixturing, mounting mechanisms, clamping devices, adhesives, and the like. Also, the sensor 16 is preferably attached to the beam 14 adjacent to the test specimen 12 such as on or integrated with any fixturing used to attach the test specimen 12 to the beam 14. Preferably, the sensor 16 generates an electronic signal proportional to the motion of the beam. The initial part of the signal has a particular time signature that can be used to characterize suddenness of the release of the loaded beam. And, as described more below, any number of sensors can be used to sense any desired test parameters of the system 10.

The breakable member 20 is preferably positioned, together with the end caps 19 and 21, between the loading device 22 and the test beam 14 so that a central axis of the breakable member 20 is coincident with the loading axis 23 of the loading device 22. The loading device 22 can then be used to load the test beam 14 in a direction along the loading axis 23 with a predetermined force that will generate a g-force having a desired magnitude when the load on the test beam 12 is released by fracturing the breakable member 20. As noted above, the test beam 14 can be loaded along the loading axis 23 in either direction (with or against the force of gravity, for example) depending on the desired test conditions. Moreover, the system 10 can be designed to load the test beam 14 in any desired direction such as in a direction that is transverse or at an angle to the gravitational force.

Figure 5:
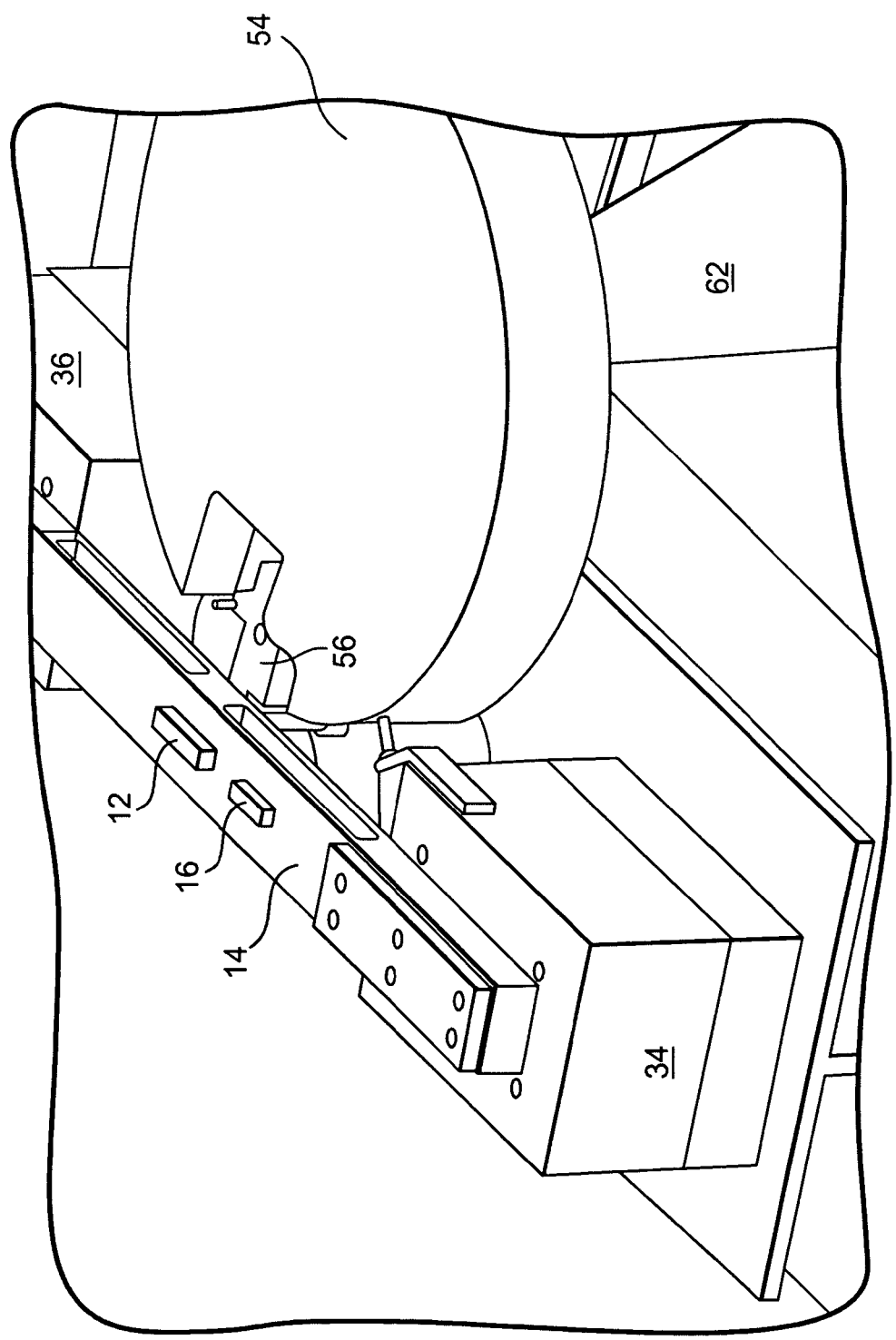
FIG. 5 is a perspective view of the system of FIG. 1, similar to FIG. 2 but viewed from a different direction, wherein the cutter is extended and just about to impact the breakable member in accordance with the present invention.

Before the flywheel 54 is rotated, the cutter 56 of the flywheel 54 is positioned in the retracted position as illustrated in FIG. 3. The flywheel 54, preferably as controlled by the control system 18 or a separate control system, is accelerated to a predetermined speed depending on the g-force desired for the particular test being conducted. When the flywheel 54 is rotating at the predetermined speed, the trigger arm 84 of the trigger 58 is extended, preferably under the control of the control system 18 (or a separate controls system) and as illustrated in FIG. 3. As the flywheel 54 rotates the trigger arm 84 of the trigger 58 impacts the toggle arm 78 of the cutter 56. When the toggle arm 78 is impacted by the trigger arm 84 the cutter 56 toggles from the retracted position shown in FIG. 3, to the extended position shown in FIGS. 2 and 5. In FIG. 4, the cutter 56 is shown rotating out of the retracted position and toward the extended position just after the toggle arm 78 has been impacted by the trigger arm 84. As the flywheel 54 continues to rotate, the cutter 56 rotates into the extended position wherein the side surface 88 of the cutter seats against the surface portion 90 of the recessed region. The impacting portion 80 of the cutter 56 can then impact the breakable member 20 to release the load on the test beam 14.

Before, during, and after the test, the control system 18 can be used to record information from the sensor 16 as well as from any other desired sensors and/or the test specimen 12 itself. For example, information related to the high g-force event such as its magnitude and duration can be recorded as well as information related to the test specimen 12 such as a performance or operational parameter.

Figure 6:
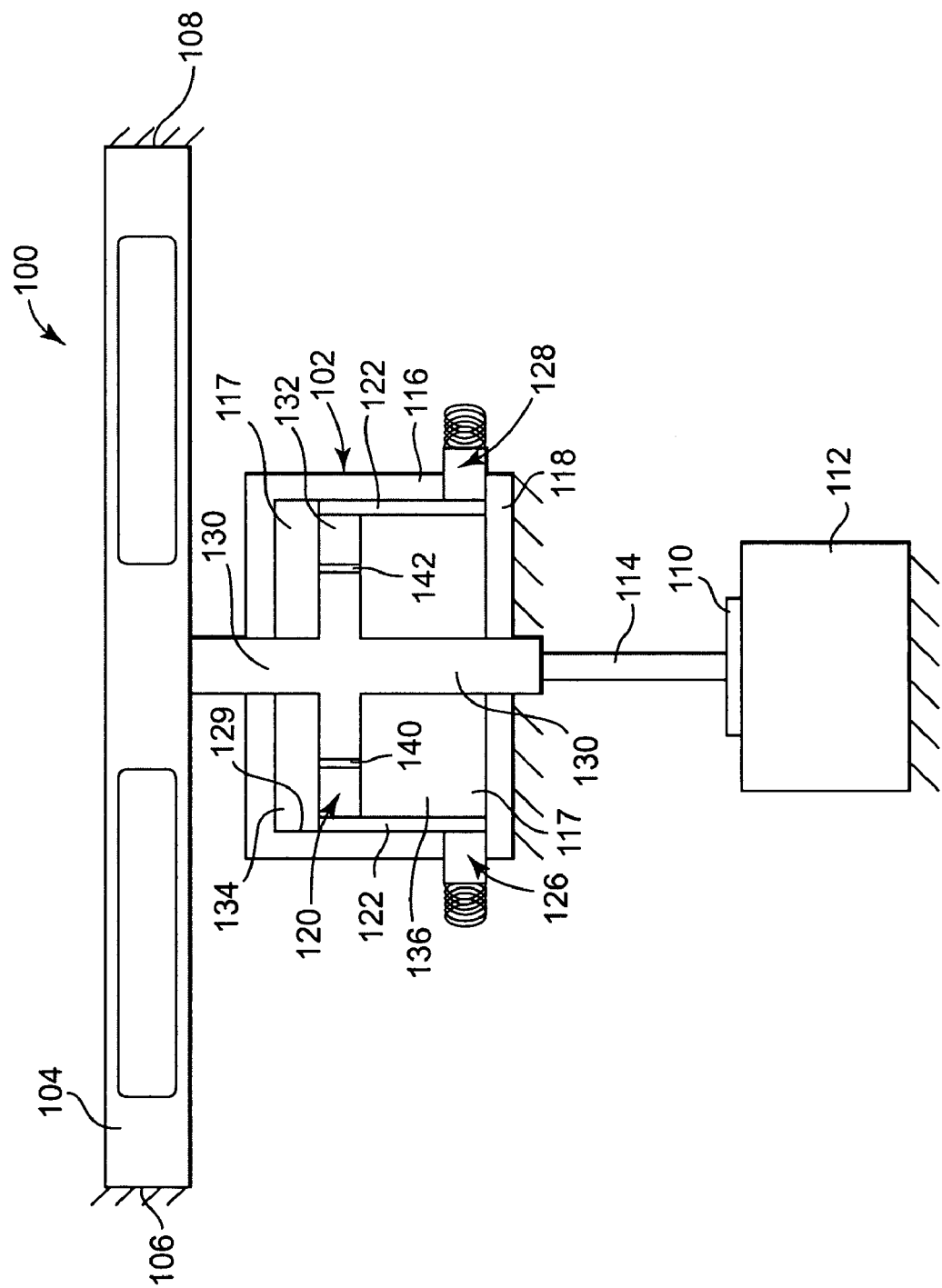
FIG. 6 is a schematic view of another system comprising a test beam in accordance with the present invention and showing in particular a damping device that can be engaged at a predetermined point during the motion of the test beam.

Another system 100 in accordance with the present invention is schematically shown in FIG. 6. The system 100 is similar to the system 10 described above except that the system 100 includes a damping device 102, which is described in more detail below. Generally, the system 100 includes a test beam 104 that is rigidly fixed at first and second ends, 106 and 108 respectively. The system 100 also comprises a loading device 110 that is functionally integrated with a beam 112. As shown in FIG. 6, a breakable member 114 is positioned between the damping device 102 and the loading device 110 in accordance with the present invention. The system 100 also preferably comprises a flywheel having a cutter (not shown in FIG. 6) but any means or device for releasing a loaded beam such as those described above or a projectile or the like can be used.

The damping device 102 of the present invention comprises a body 116 having an internal space 117, preferably cylindrical, that is filled with a hydraulic fluid. The body 116 is preferably mounted to a frame structure 118 or the like, as schematically illustrated. The damping device also includes a piston 120, a sleeve 122, and first and second latching devices, 126 and 128, that function to restrict the motion of the sleeve 122 in accordance with the present invention as described in further detail below.

The piston 120, as shown, preferably comprises a shaft 130 and a plate 132. The shaft 130 is preferably capable of transferring the force applied to the breakable member 114 by the loading device 110 to the test beam 104. As shown, the plate 132 defines a volume of hydraulic fluid above the plate 134 and a volume of hydraulic fluid 136 below the plate 134. The plate 132 also preferably includes first and second openings, 140 and 142, respectively, that can controllably restrict the rate of flow of hydraulic fluid to flow from one side of the plate 132 to the other.

The damping device 102 is preferably designed to contain the hydraulic fluid within the body 116 of the damping device 102. Preferably, the body 116, sleeve 122, shaft 130, and plate 132 are designed so that there is a sliding seal between the plate 132, sleeve 122, and an inside surface 129 of the body 116. Moreover, the shaft 130 is preferably designed to form a sliding seal with the body 116.

Figure 7:
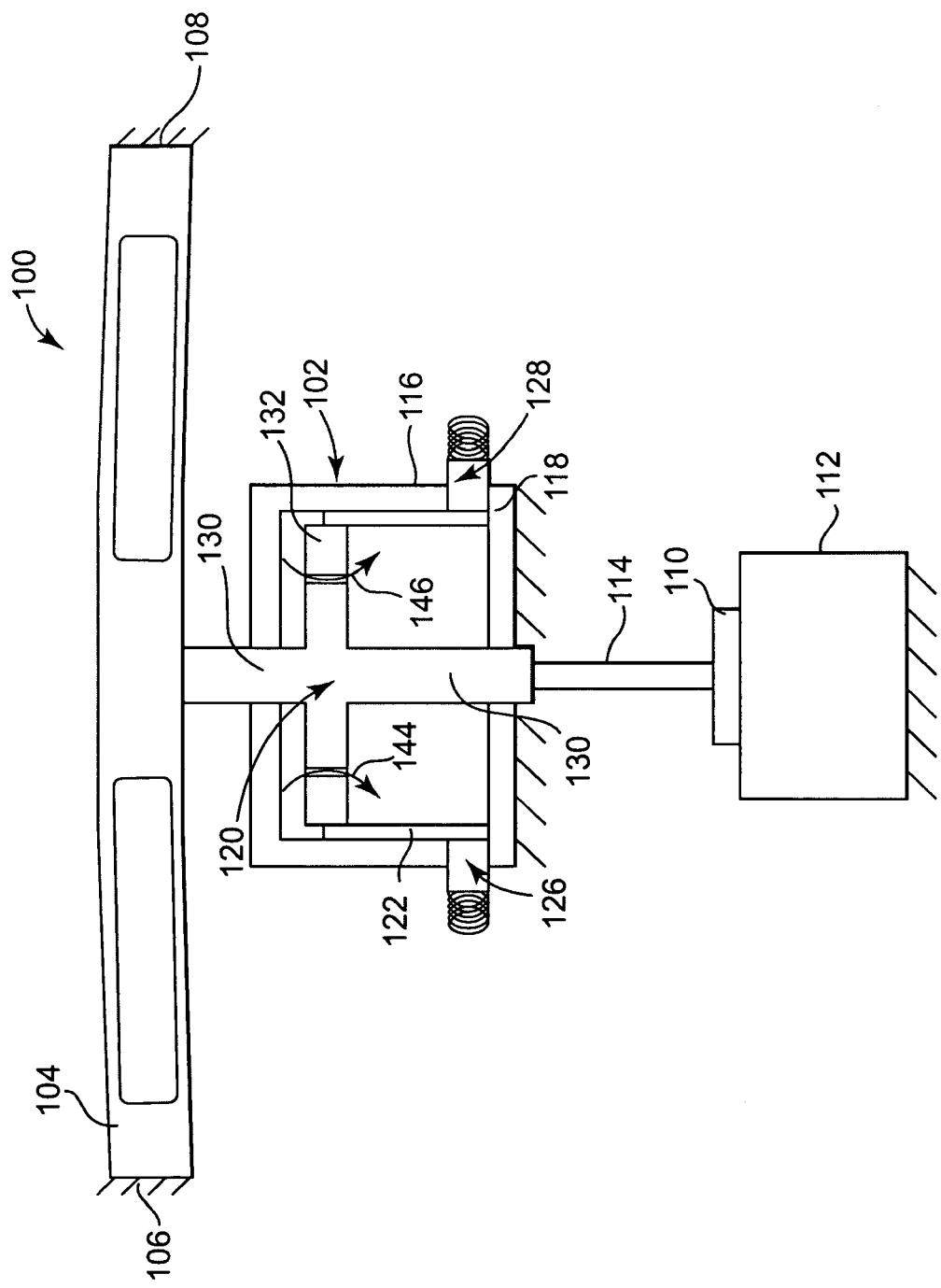
FIG. 7 shows the system of FIG. 6 wherein the test beam is partially loaded and the damping device is disengaged and not providing a damping function.

In FIG. 7, the test beam 104 is shown as partially loaded by the loading device 110. As the loading device 110 drives the breakable member 114 upwardly, as illustrated, the breakable member 114 drives the piston 120 upwardly as well. The test beam 104 is preferably loaded at a speed so that as the plate 132 moves upwardly, hydraulic fluid can readily flow through the openings, 140 and 142, as schematically shown by the arrows identified with reference numerals 144 and 146, respectively, without any damping action.

Figure 8:
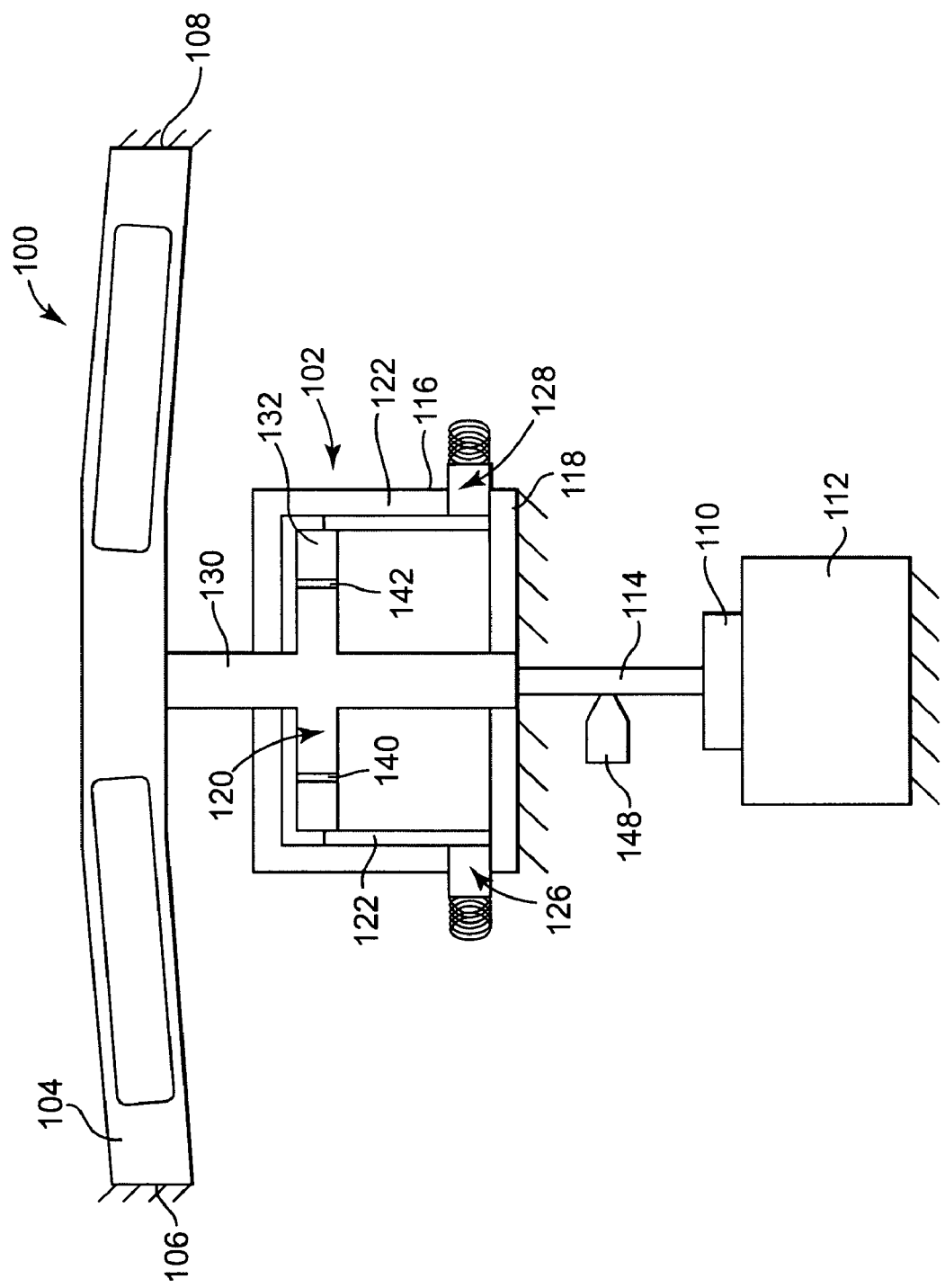
FIG. 8 shows the system of FIG. 6 wherein the test beam is fully loaded, the damping device is disengaged, and at a point in time just before a cutter breaks a breakable member to release the load on the test beam.

In FIG. 8, the test beam 104 is shown in a loaded state and ready to be released to provide a high g-force test event by a cutter 148, as schematically illustrated. Preferably, cutter 148 is associated with a controllably movable device or body such as a flywheel or the like as described above. A projectile may also be used. In this configuration, no hydraulic fluid is flowing across the plate 132. Here, the damping device 102 is at a steady state.

Figure 9:
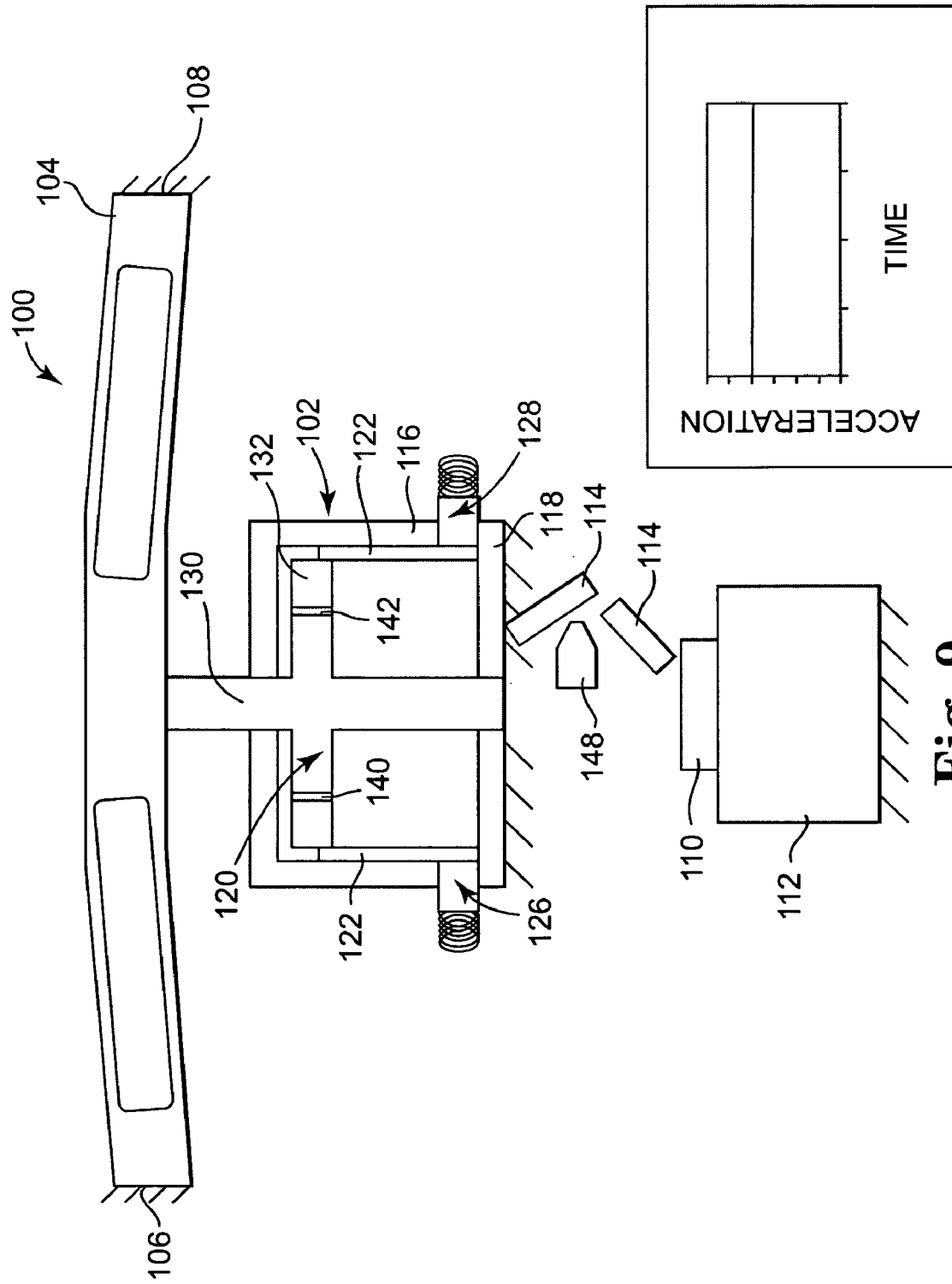
FIG. 9 shows the system of FIG. 8 at the point where the cutter breaks the breakable member and suddenly releases the load on the test beam.

In FIG. 9, the cutter 148 is shown breaking the breakable member 114 and releasing the load on the test beam 104. FIG. 9 also includes a plot of test beam acceleration with respect to time. At the instant in time that the load on the test beam 104 is released (time equal to zero), the acceleration of the test beam 104 is also zero.

Figure 10:
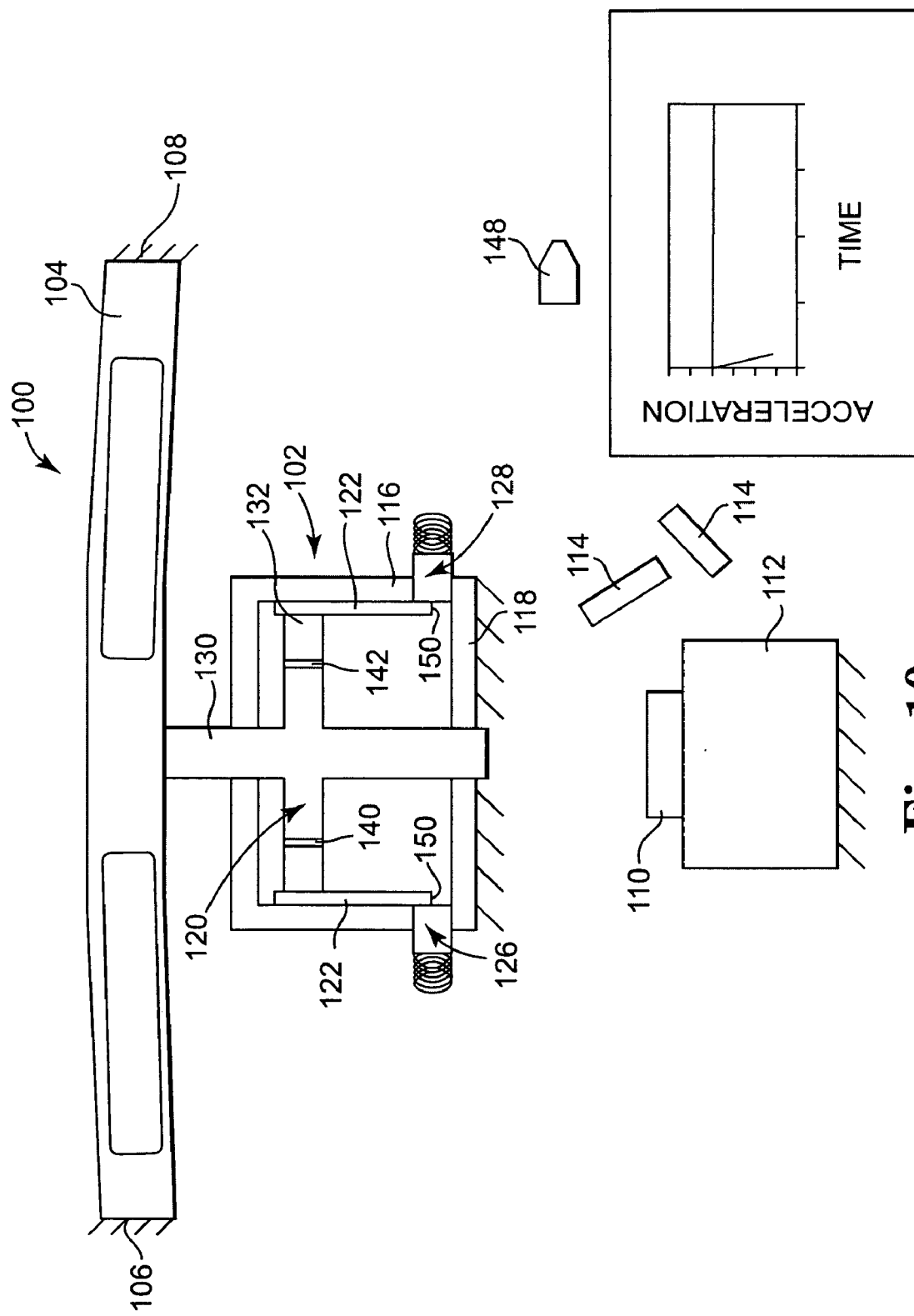
FIG. 10 shows a first portion of the first half-cycle of the motion of the test beam after the load on the test beam is released.

In FIG. 10, the test beam 104 has accelerated in a downward direction from the position shown in FIG. 9. The downward motion of the test beam 104 forces the piston 120 downward as well. As the piston 120 moves downward, the openings, 140 and 142, in the plate 132 restrict the flow of hydraulic fluid through the plate 132. This would otherwise have a damping affect except that the sleeve 122 is designed to be able to move upwardly (opposite the direction of the piston 120) to accommodate the hydraulic fluid that is displaced by the downwardly moving plate 132.

The hydraulic fluid displaced by the downwardly moving plate 132 forces the sleeve 122 upward until an end 150 of the sleeve 122 passes the latching devices, 126 and 128, as illustrated in FIG. 11. At this point, the latching devices, 126 and 128, capture the sleeve 122 and prevent the sleeve 122 from returning to its initial position. The latching devices, 126 and 128, preferably comprise spring-loaded pins or the like. Any functionally equivalent device or mechanism that is capable of locking the sleeve 122 in accordance with the present invention can be used for the latching devices, 126 and 128. Preferably, the sleeve 122 is latched when the acceleration of the test beam 104 is zero, as shown. That is, the sleeve 122 is preferably latched after the test beam 104 has moved through the first half-cycle of the oscillation of the test beam 104.

Figure 12:
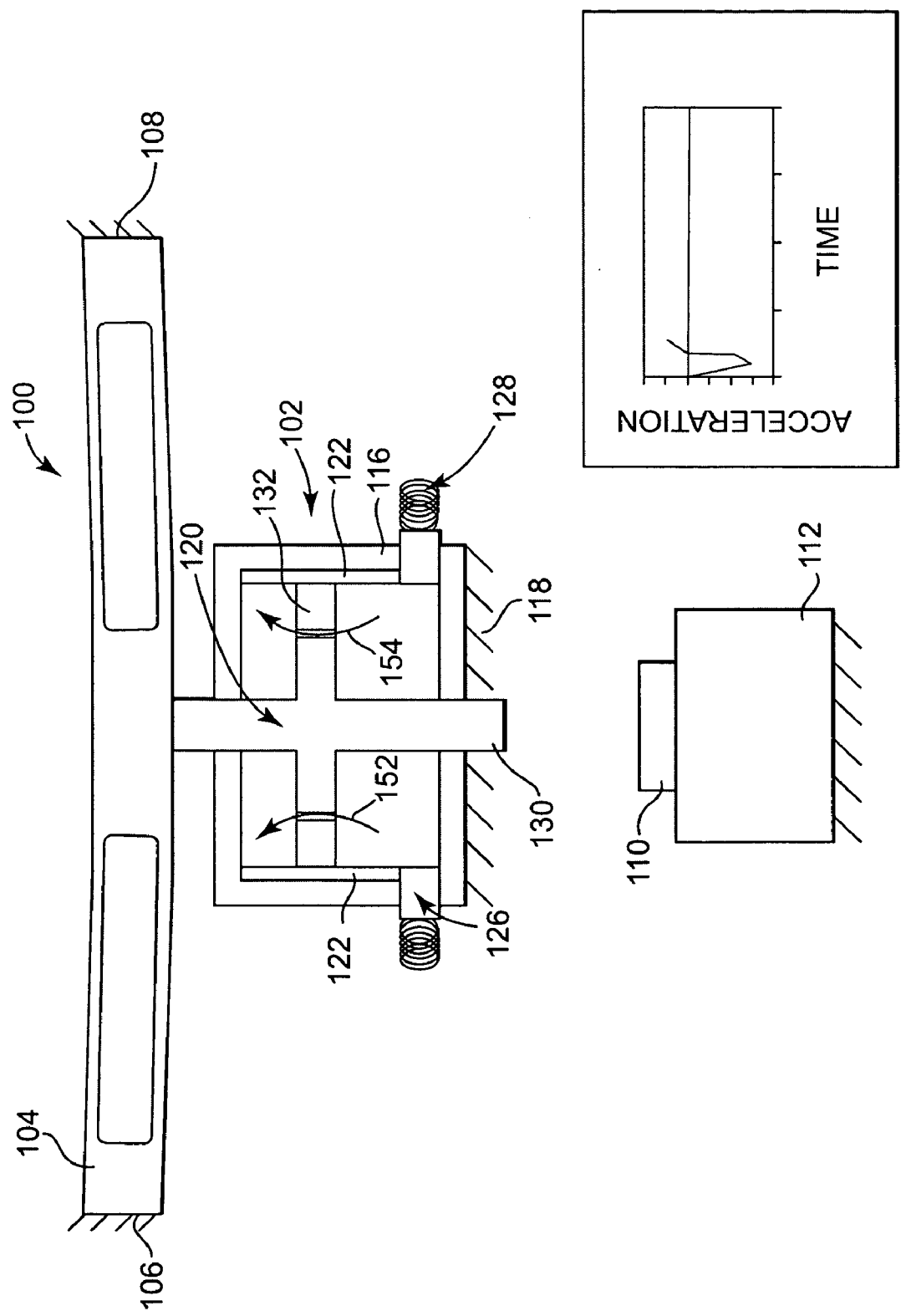
FIGS. 12 and 13 show the second half-cycle of the motion of the test beam with the damping device engaged and providing a damping function.
Figure 13:
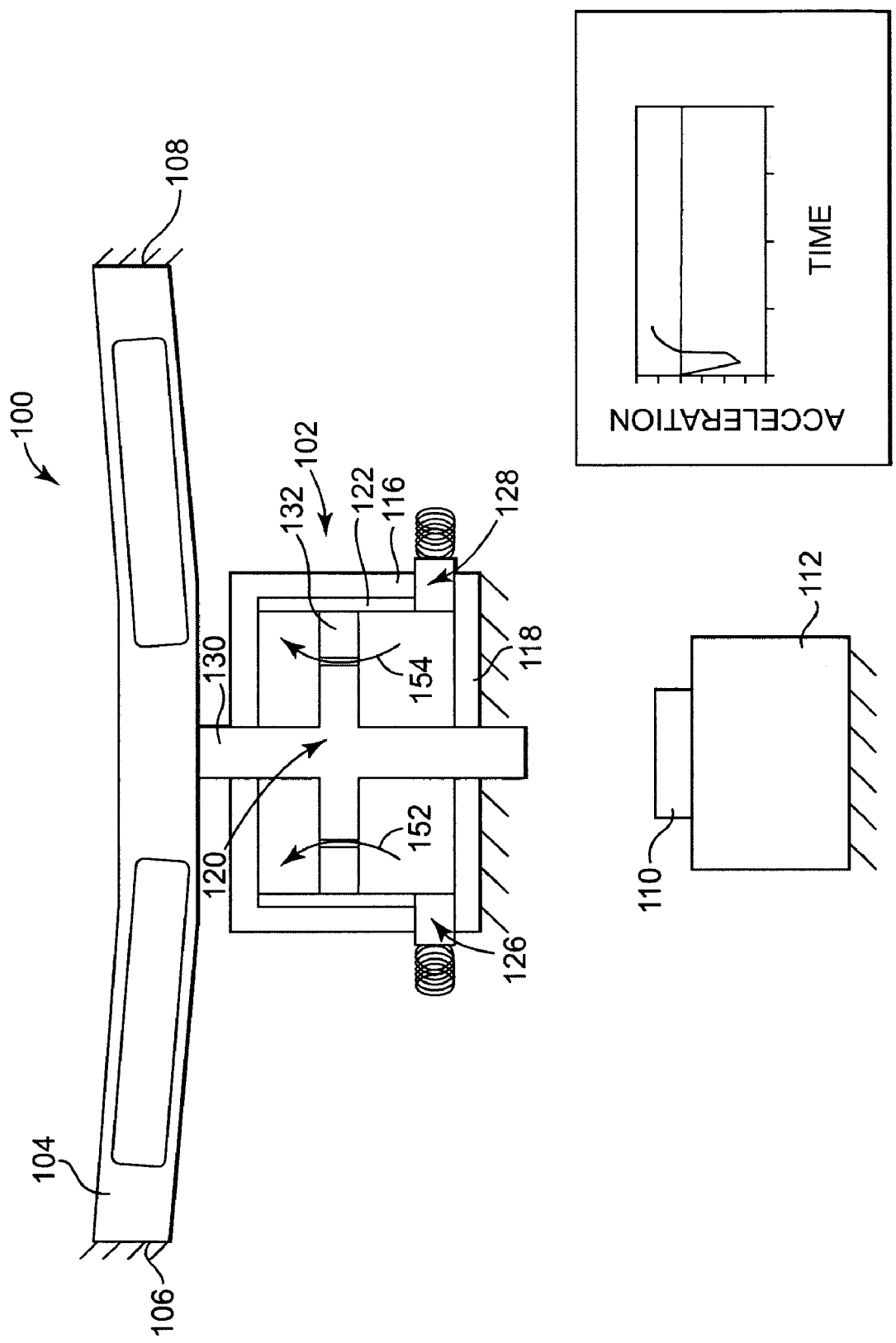
Figure 15:
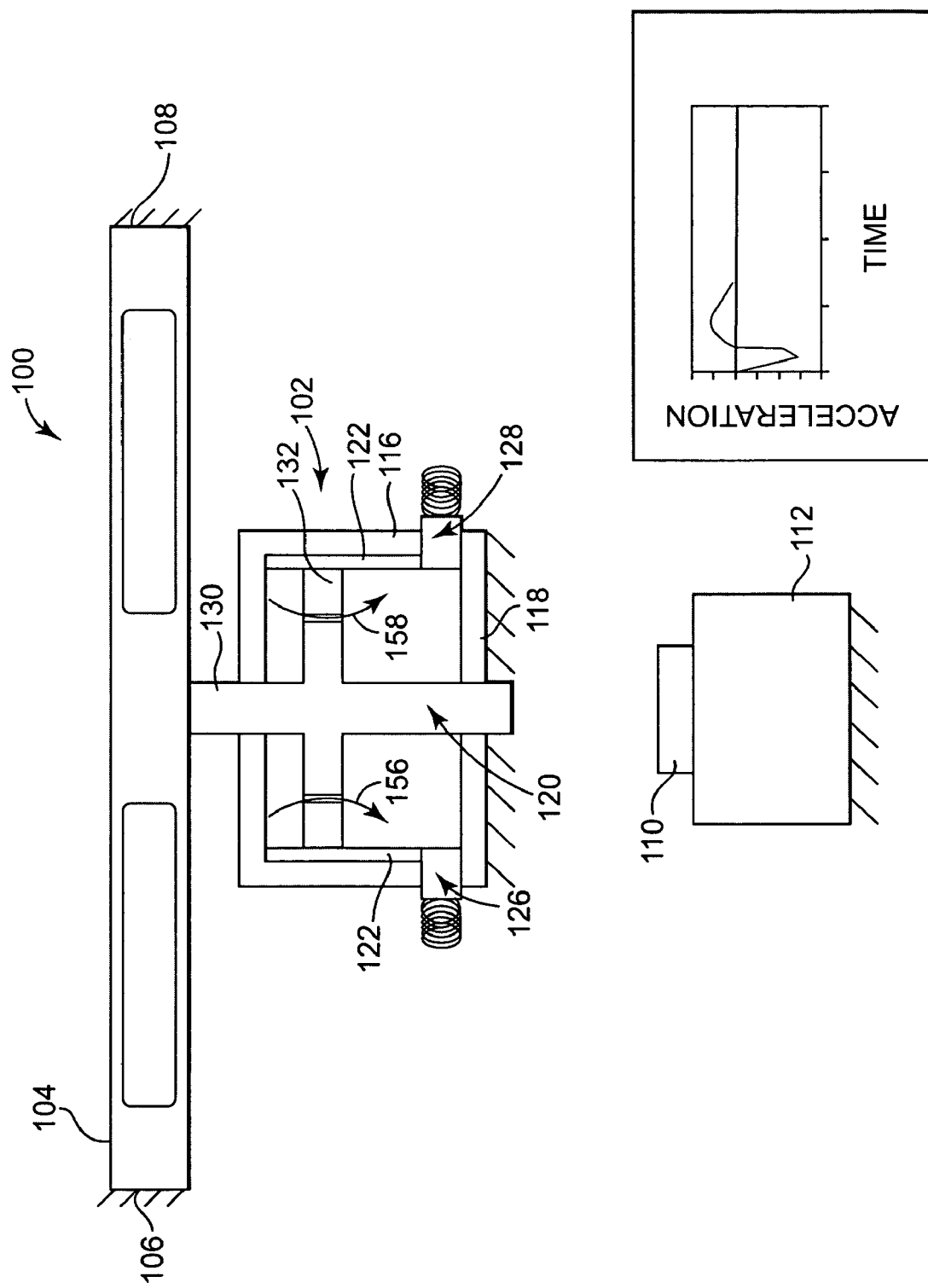
Figure 16:
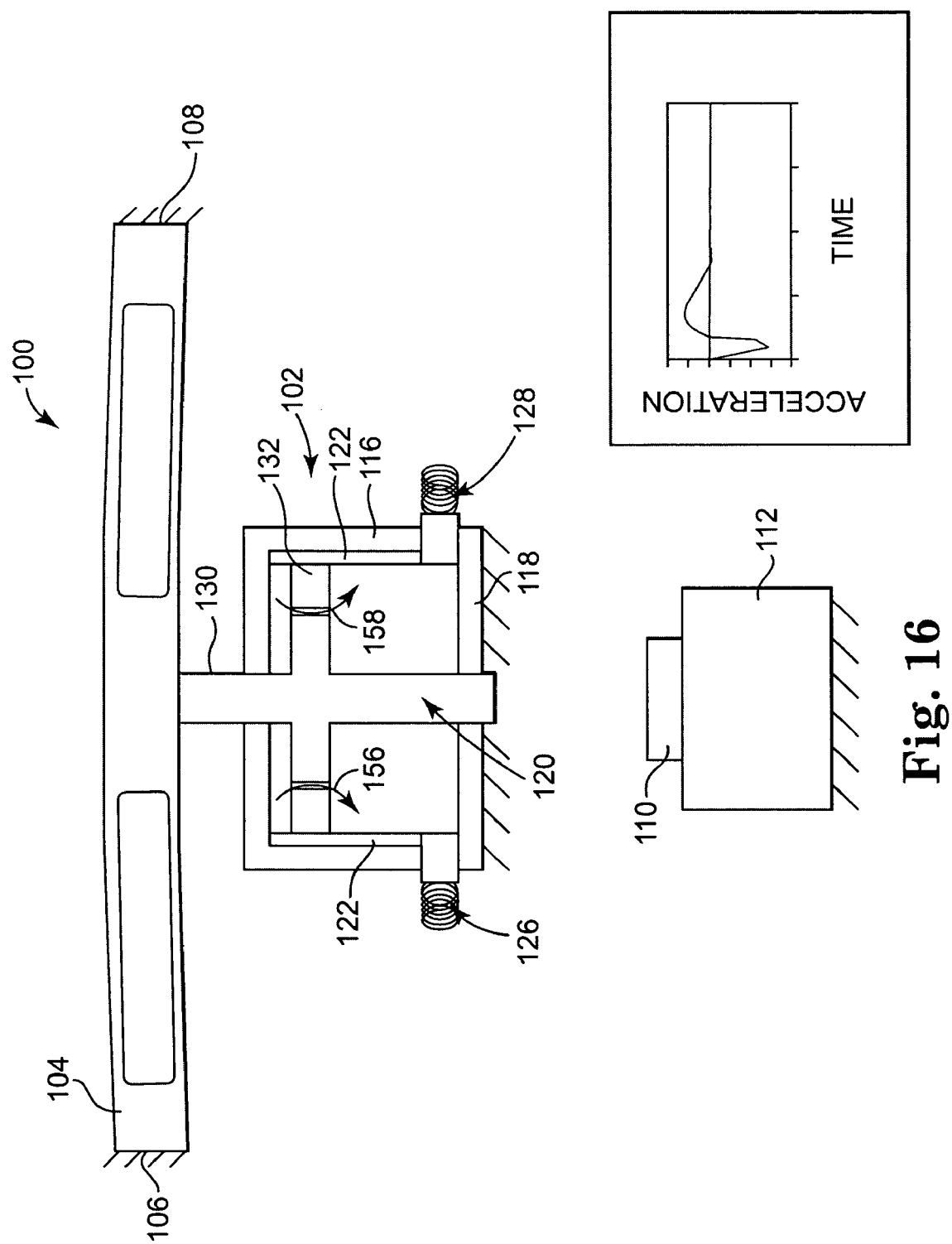
FIGS. 16 and 17 show a final half-cycle of the motion of the test beam with the damping device engaged and providing a damping function that brings the test beam to rest.
Figure 17:
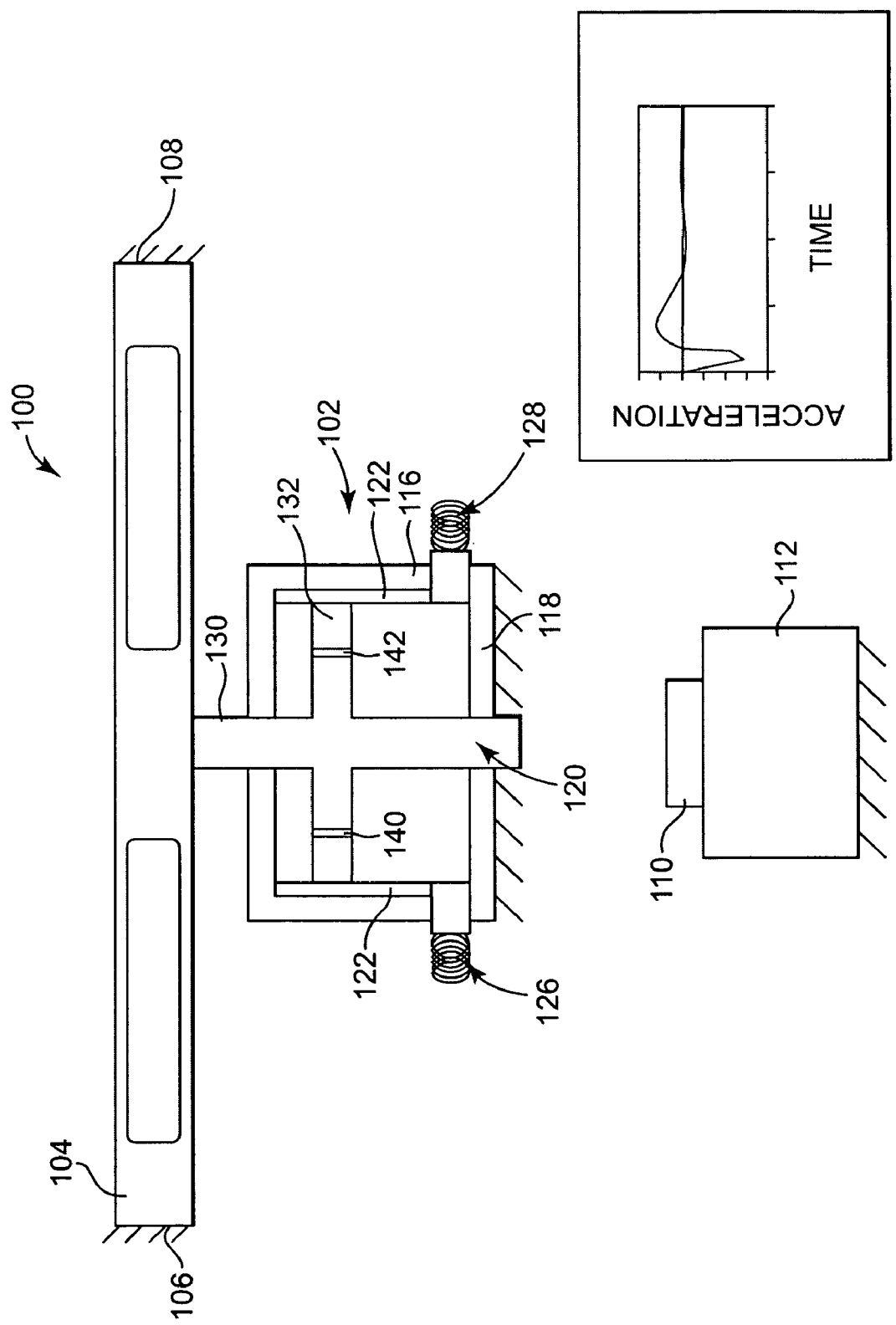

After the sleeve 122 has been latched, the damping device 100 preferably functions to dampen the subsequent oscillation of the test beam 104 as illustrated in FIG. 12-17. In FIGS. 12 and 13, the second half-cycle of the oscillation of the test beam 104 is shown. As the test beam 104 forces the plate 132 downwardly, the openings, 140 and 142, restrict the flow of hydraulic fluid through the plate 132 as illustrated by the arrows indicated by reference numerals 152 and 154, respectively. In FIGS. 14 and 15, the third half-cycle of the oscillation of the test beam 104 is shown. As above, as the test beam 104 pulls the plate 132 upwardly, the openings, 140 and 142, restrict the flow of hydraulic fluid through the plate 132 as illustrated by the arrows indicated by reference numerals 156 and 158, respectively. A final half-cycle of the test beam 104 is shown in FIGS. 16 and 17. Here the damping of the oscillation of the test beam is completed. As the test beam 104 forces the plate 132 downwardly, the openings, 140 and 142, restrict the flow of hydraulic fluid through the plate 132 as illustrated by the arrows indicated by reference numerals 160 and 162, respectively.

Methods and systems for high g-force testing are also disclosed in Applicant's copending patent application filed on even date herewith, entitled "HIGH G-FORCE SHOCK PULSE GENERATOR SYSTEMS AND METHODS," and having attorney docket number H0006556-1632US (HON0007/US), the entire disclosure of which is incorporated by reference herein for all purposes.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A method for applying a high g-force to a test specimen, the method comprising the steps of:
   rigidly fixing an end of a beam;
   mounting a test specimen on the beam at a first predetermined location with respect to the rigidly fixed end of the beam;
   applying a force to the beam with a loading device, a breakable loading member between the loading device and the beam, said force applied at a second predetermined location with respect to the rigidly fixed end of the beam to elastically strain the beam by a predetermined amount;
   releasing the force applied to the beam by the loading device; and
   engaging the beam with a damper at a predetermined point after the beam reaches maximum displacement, after the force applied to the beam is released.

2. The method of claim 1, further comprising the step of rigidly fixing a second end of the beam.

3. The method of claim 1, wherein the breakable loading member comprises a ceramic column.

4. The method of claim 1, wherein the step of releasing the force applied to the beam by the loading device comprises impacting the breakable loading member with a projectile.

5. A system for applying a high g-force to a test specimen, the system comprising:
- a beam rigidly fixed at an end, the beam capable of having a test specimen mounted on the beam at a first predetermined location from the rigidly fixed end of the beam;
- a loading device that can apply a force to the beam at a second predetermined location with respect to the rigidly fixed end of the beam to elastically strain the beam by a predetermined amount;
- means for controllably releasing the force applied to the beam by the loading device; and
- a damper operatively connected to the beam, the damper positioned on a loading axis of the loading device between the loading device and the beam, the damper, engageable at a predetermined point after releasing the force applied to the beam.

6. The system of claim 5, wherein the damper comprises a body having an internal space having a piston and a sleeve that can slide within the body.

7. The system of claim 6, wherein the damper comprises a controllably engageable latching device that can prevent the sleeve from sliding within the body when engaged.

8. The system of claim 7, wherein the latching device of the damper comprises at least one spring loaded pin.

9. The system of claim 5, wherein the beam is rigidly fixed at first and second ends of the beam.

10. The system of claim 5, wherein the loading device comprises a hydraulic ram.

11. The system of claim 5, comprising a breakable loading member that can be positioned between the loading device and the beam to apply the force to the beam.

12. The system of claim 11, wherein the breakable loading member comprises a ceramic column.

13. The system of claim 5, wherein the means for controllably releasing the force applied to the beam comprises a projectile can impact the breakable loading member when the breakable loading member is positioned between the loading device and the beam.

14. A system for applying a high g-force to a test specimen, the system comprising:
- a beam rigidly fixed at an end, the beam capable of having a test specimen mounted on the beam at a first predetermined location from the rigidly fixed end of the beam;
- a loading device comprising a breakable loading member, wherein the loading device can apply a force to the beam with the breakable loading member at a second predetermined location with respect to the rigidly fixed end of the beam to elastically strain the beam by a predetermined amount;
- means for breaking the breakable loading member to release a force on the beam when loaded with the loading device; and
- a damper operatively connected to the beam, the damper positioned on a loading axis of the loading device between the loading device and the beam, the damper, engageable at a predetermined point after breaking the breakable loading member to release the beam when loaded by the loading device.

15. The system of claim 14, wherein the damper comprises a body having an internal space having a piston and a sleeve that can slide within the body.

16. The system of claim 15, wherein the damper comprises a controllably engageable latching device that can prevent the sleeve from sliding within the body when engaged.

17. The system of claim 15, wherein the means for controllably releasing the force applied to the beam comprises a projectile can impact the breakable loading member when the breakable loading member is positioned between the loading device and the beam.

* * * * *